United States Patent [19]

Donelan

[11] Patent Number: 5,368,050
[45] Date of Patent: Nov. 29, 1994

[54] RAPE PREVENTION DEVICE

[76] Inventor: John P. Donelan, 40 Highland Dr., Centerville, Mass. 02632

[21] Appl. No.: 114,484

[22] Filed: Aug. 31, 1993

[51] Int. Cl.⁵ .......................... A41B 9/00; A41B 9/12; A61F 13/00
[52] U.S. Cl. .................................. 128/884; 128/883; 128/891; 602/70; 2/400; 2/406
[58] Field of Search .................. 2/1, 2, 300, 310, 311, 2/312, 338, 400, 401, 402, 403, 406; 128/883, 884, 888, 891; 602/24, 70, 71, 72; 604/386, 393, 394; 450/150, 155, 140, 144, 153, 147, 148, 102, 103, 104

[56] References Cited

U.S. PATENT DOCUMENTS

| | | | |
|---|---|---|---|
| 875,845 | 1/1908 | Perkins | 128/883 |
| 1,144,253 | 6/1915 | Rubel | 604/394 |
| 1,477,187 | 12/1923 | Rayne | 602/73 X |
| 2,691,984 | 10/1954 | Zacks | 604/394 X |
| 3,227,160 | 1/1966 | Younger | 602/70 X |
| 5,174,307 | 12/1992 | Thompson | 602/70 X |

FOREIGN PATENT DOCUMENTS 175799  1/1953  Austria ..................... 2/321

Primary Examiner—Jeanette E. Chapman
Attorney, Agent, or Firm—Samuels, Gauthier & Stevens

[57] ABSTRACT

A rape prevention device including a belt adapted to encircle the waist of a wearer and a shield portion extending through the legs and crotch of the wearer from a rear region of the belt to a front region of the belt. The shield portion includes a plurality of shield segments adapted to cover the genitalia of the wearer.

11 Claims, 4 Drawing Sheets

RAPE PREVENTION DEVICE

BACKGROUND OF THE INVENTION

The invention relates to a rape prevention device.

The use of a garment to enhance rape prevention is preferable for women rather than the use of weapons. Oftentimes the weapon can in fact be turned against the user, thus defeating the purpose of the weapon as a deterrent.

Unfortunately, conventional chastity undergarments are particularly ineffective as they are either easily removed or so cumbersome as to be uncomfortable to the wearer.

It is therefore an object of the present invention to provide a rape prevention device which may be worn as an undergarment and which is effective in covering the genitalia of the wearer and not easily removed by an attacker.

SUMMARY OF THE INVENTION

Accordingly, the present invention provides a rape prevention device having a belt adapted to encircle the waist of a wearer, the belt having a front region and a rear region. A shield portion is provided to extend through the legs and crotch of the wearer from a rear end coupled to the rear region of the belt to a front end coupled to the front region of the belt. The shield portion includes a plurality of shield segments adapted to cover the genitalia of the wearer.

DETAILED DESCRIPTION OF THE ILLUSTRATED EMBODIMENTS

Figure 1:
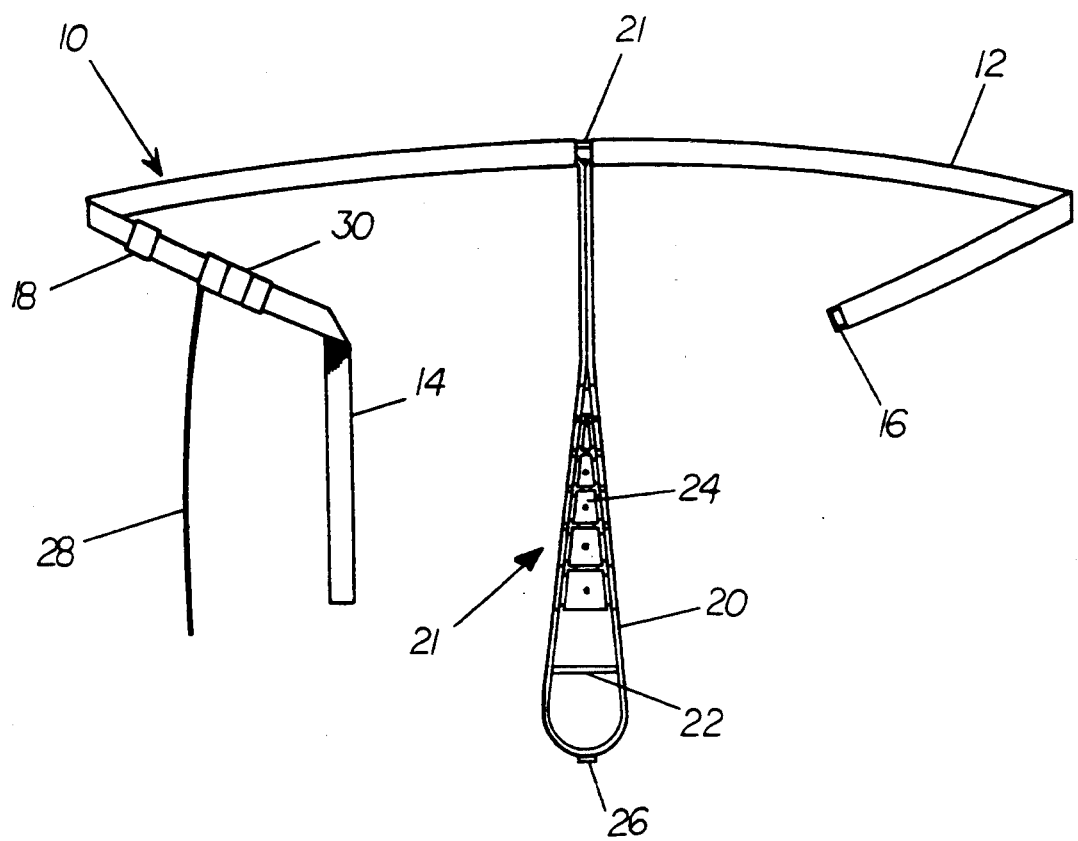
FIG. 1 shows a perspective view of the rape prevention device according to the present invention.

With reference now to FIG. 1, a rape prevention device 10 in accordance with the present invention is shown. The device includes a belt 12 adapted to encircle the waist of a wearer. A waist adjustment strap 14 is provided at one end of the belt 12 for interengagement with a strap support ring 16 so that the belt is adjustable to the specific waist size of the wearer. The adjustment strap 14 is routed through the strap support ring 16 and doubled back through a strap adjustment locking unit 18. The wearer may adjust the belt by pulling the adjustment strap 14 so as to compress the waist belt together evenly so as to secure it over the hips.

Figure 3:
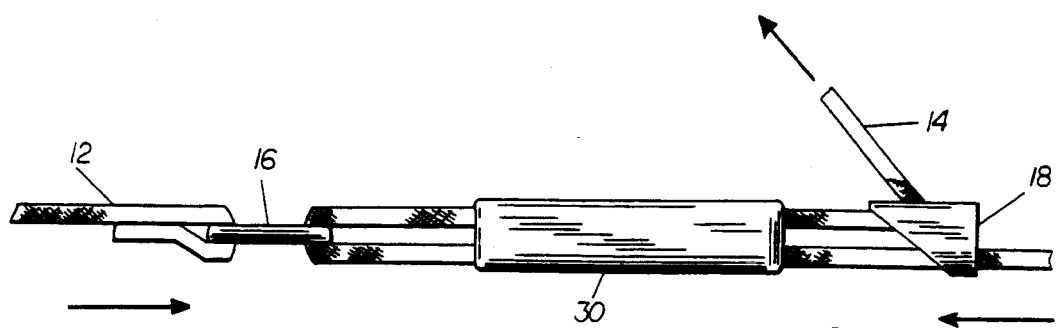
FIG. 3 shows a top plan view of the frontal region of the belt and components for tightening the belt of the rape prevention device.

With reference to FIG. 3, directional arrows are provided to indicate the direction each half of the waist belt moves when the adjustment strap is pulled tight. The locking unit 18 includes a ratchet lock mechanism which automatically activates and secures the belt at any desired point. A limiting device on the strap prevents the belt from being tightened beyond a predetermined point, thus stopping an attacker from tightening the strap to inhibit breathing or movement of the wearer.

With the belt 12 secure, a line locking unit 30 which slides into position over the doubled back adjustment strap at a center portion of the front region of the belt. The line locking unit 30 is slidable along the doubled back portion of the adjustment strap by pressing, for example, two buttons to allow movement thereof. When the buttons are released, the locking unit grips the belt securely at that position. When the locking unit is engaged, the buttons become inoperable, thus preventing forced removal of the belt.

Referring once again to FIG. 1, a shield support loop 20 is fixedly attached to a rear portion of the belt 12 by a support loop anchor 21. The support loop 20 is preferably made of wire and serves as the frame for the shield portion 23 of the device. The shield portion includes a support bar 22 which prevents collapse of the shield portion if the front of the belt is pulled or twisted. In addition, a plurality of adjustable shield plates 24 are supported between opposite sides of the shield support loop 20. The adjustable shield plates serve as an impenetrable shield which covers the genitalia of the wearer. At the front end of the loop 20 there is provided a pulley mechanism 26 which serves to support the shield portion 23 within the crotch of the wearer.

Figure 2:
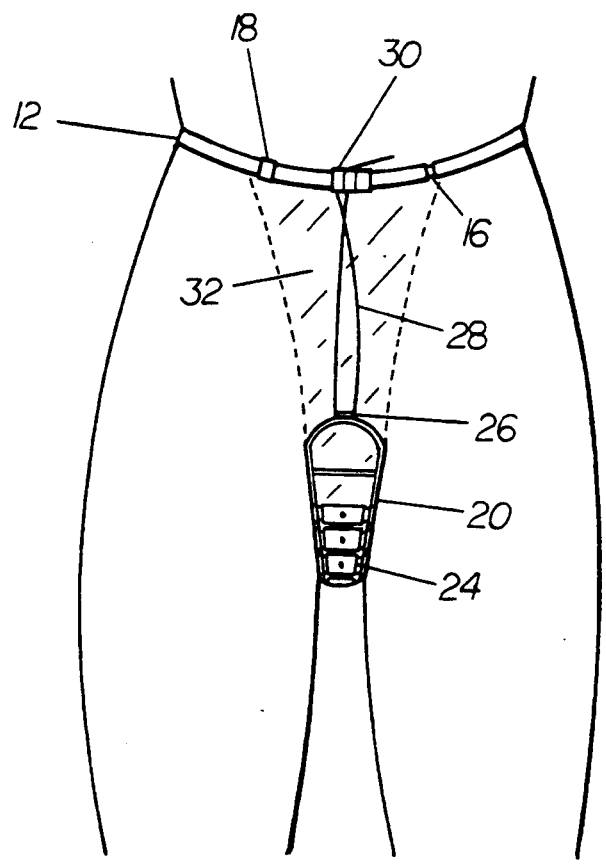
FIG. 2 shows a perspective view of the rape prevention device as worn by a wearer.

With respect to FIG. 2, the device 10 is shown as worn around the waist of a wearer. The shield adjust line 28 is passed through the cylinder 26 to form a loop after the adjust line is passed back through the line locking unit 30. As the adjust line 28 is tightened at the waist, the cylinder 26 serves as a pulley, thus tightening the shield portion 23 by pulling it upwards towards the waist, while the front of the waist belt pulls down slightly. As the shield support loop 20 is pulled upwards, the ratchet action of the line locking unit 30 holds it in place.

Once the device is fastened, the narrow configuration of the shield support loop 20 ensures that physical movement is not impaired. The waist belt 12, secure to the hips, provides leverage for the locking unit 30, and cannot be pulled off when locked in position. Both the waist belt 12 and the support loop 20 are drawn towards one another during the tightening process, effectively sandwiching the shield plates 24 to the body. A fabric enclosure 32 may be utilized to provide greater comfort and better aesthetics for the device.

Figure 4:
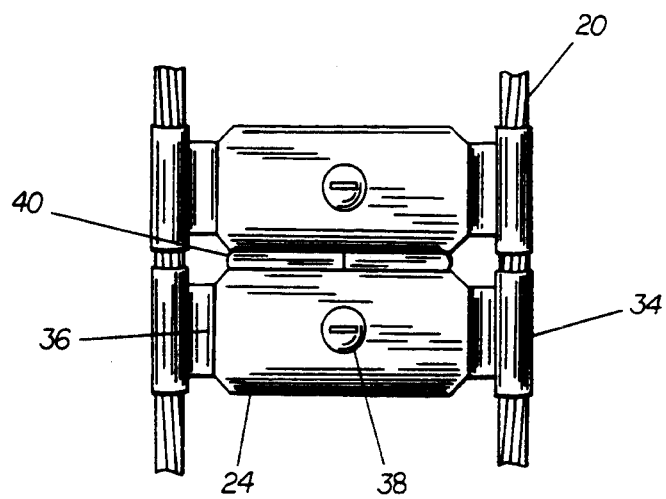
FIG. 4 shows shield segments utilized in the rape prevention device.

FIG. 4 shows a perspective view of the adjustable shield plates 24 as they are supported by the shield support loop 20. Each of the plates 24 include oppositely disposed support cylinders 34 at the end of adjustable support arms 36. The shield support loop 20 passes through each of the support cylinders 34 to suspend the plates between the opposite sides of the loop. The adjustable support arms 36 may be retracted or extended by adjusting a flush screw 38 in order to properly size the shield plate to the particular wearer. In addition, each of the shield plates are connected to one another by a hinge 40 so as to allow freedom of movement in only the vertical plane, thus allowing movements such as sitting without discomfort. Once the device 12 is secured in place, the shield plates 24 prevent exposures of the crotch area and thus the genitalia of the wearer, since the support loop 20 anchors the plates firmly to the body.

Figure 5:
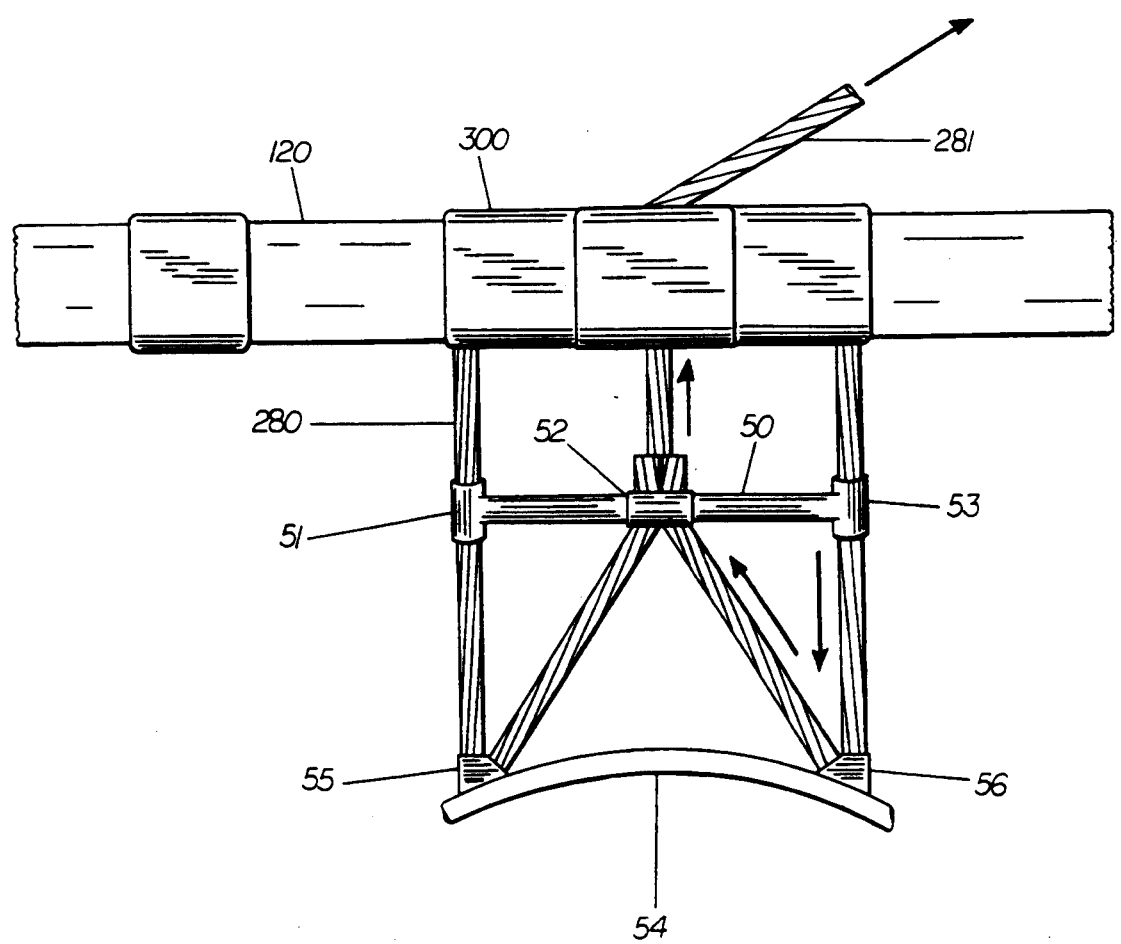
FIG. 5 shows a frontal view of an alternate embodiment of the rape prevention device according to the present invention.

According to an alternate embodiment of the present invention as shown in FIG. 5, a waist belt 120 includes a locking unit 300 for tightening the belt around the waist of the wearer. In addition, a rigid support bar 50 and curved support bar 54 are provided for accommodating the tightening the support loop 20 within the crotch of the wearer. A shield adjust line 280 is provided as anchored on opposite ends of the locking unit 300 and passed through holes 51 and 53 disposed on opposite ends of the support bar 50. The line 280 continues through oppositely disposed cylinders 55 and 56 on the curved support bar 54, and is passed back through a center support through-hole 52. A portion 281 of the line 280 is passed through the locking mechanism 300 for tightening the support loop 20 which is coupled to the curved support bar 54. This configuration enhances prevention of twisting the support loop 20 within the crotch of the wearer.

The foregoing description has been set forth to illustrate the invention and is not intended to be limiting. Since modifications of the described embodiments incorporating the spirit and substance of the invention may occur to persons skilled in the art, the scope of the invention should be limited soley with reference to the appended claims and equivalents thereof.

I claim:

1. A rape prevention device comprising:
   a belt adapted to encircle the waist of a wearer, said belt having a front region and a rear region; and
   a shield portion extending through the legs and crotch of the wearer from a rear end coupled to said rear region of said belt to a front end coupled to said front region of said belt, said shield portion including a plurality of shield segments which are pivotably coupled to adjacent segments and adapted to cover the genitalia of the wearer,
   said shield portion comprises a compliant loop line coupled to the rear portion of said belt; and
   said shield segments comprise support members which suspend said segments from opposite sides of said loop line.

2. The device of claim 1, wherein each of said shield segments comprise means for adjusting the width of said segment to accommodate sizing to the wearer.

3. The device of claim 1 further comprising coupling means for adjustably coupling said front end of said shield portion to said front region of said belt so as to tighten said shield portion within the crotch of the wearer.

4. The device of claim 3, wherein said coupling means comprises pulley means disposed at said front end of said shield portion, a locking mechanism disposed at said front region of said belt, and a tightening line affixed to said front region of said belt which is passed through said pulley means and back through said locking mechanism in order to tightly secure said shield portion within the crotch of the wearer.

5. The device of claim 3, wherein said coupling means comprises first and second pulley means disposed at said front end of said shield portion, a locking mechanism disposed at said front region of said belt, and first and second tightening lines affixed to said front region of said belt which are respectively passed through said first and second pulley means and back through said locking mechanism in order to tightly secure said shield portion within the crotch of the wearer.

6. The device of claim 5, wherein said coupling means further comprises a support member adapted to space apart said first and second tightening lines prior to passage through said first and second pulley means and to align said tightening lines after passage through said pulley means for passage to said locking mechanism so as to prevent twisting of said shield portion within the crotch of the wearer.

7. The device of claim 1, wherein said shield portion and plurality of shield segments are contained within a pliable housing.

8. A rape prevention device comprising:
   a belt which is worn around the waist of a wearer;
   first coupling means associated with a front section of said belt for coupling the belt ends and accommodating tightening of said belt;
   a shield component extending through the crotch of the wearer from a fixed position with a rear section of said belt member to said front section, said shield component comprising a compliant wire loop;
   a plurality of shield segments are pivotally coupled to adjacent segments and are supported by said shield component, said shield segments adapted to cover the genitalia of the wearer;
   said shield segments comprise support members which suspend said segments from opposite sides of said compliant wire loop; and
   second coupling means for coupling the front end of said shield component to said front section of said belt, said second coupling means being adjustable so as to tighten said shield component within the crotch of the wearer.

9. The device of claim 8, wherein said shield segments comprise coupling members for coupling the segments to opposite sides of said loop.

10. The device of claim 9, wherein said coupling members are adjustable so as to vary the width of said shield segments.

11. The device of claim 8, wherein said second coupling means comprise means for inhibiting twisting of said shield component within the crotch of the wearer.

* * * * *